United States Patent [19]

Dubois et al.

[11] Patent Number: 6,126,930
[45] Date of Patent: *Oct. 3, 2000

[54] SPRAY COMPOSITIONS

[75] Inventors: Zerlina Guzdar Dubois, Mason; Amber Kathleen Tanner, Maineville, both of Ohio

[73] Assignee: The Procter & Gamble Company, Cincinnati, Ohio

[ * ] Notice: This patent is subject to a terminal disclaimer.

[21] Appl. No.: 08/800,935

[22] Filed: Feb. 13, 1997

[51] Int. Cl.[7] ............... A61K 7/15; A61K 7/06; A61K 7/46; A61R 21/00
[52] U.S. Cl. ............... 424/73; 424/401; 424/70; 514/1; 514/847; 514/848; 514/2
[58] Field of Search ............... 514/2, 1, 847, 514/848; 424/70, 73, 401

[56] References Cited

U.S. PATENT DOCUMENTS

| | | | |
|---|---|---|---|
| 4,278,658 | 7/1981 | Hooper et al. | 424/65 |
| 4,650,602 | 3/1987 | Schieferstein | 252/522 R |
| 5,449,512 | 9/1995 | Simmons | 424/73 |

FOREIGN PATENT DOCUMENTS

| | | | |
|---|---|---|---|
| 0 545 556 A2 | 6/1992 | European Pat. Off. | |
| 0 684 038 A2 | 3/1995 | European Pat. Off. | |
| 08187277A | 7/1996 | Japan | A61L 9/00 |
| 08188791A | 7/1996 | Japan | C11B 9/00 |
| 08188792A | 7/1996 | Japan | C11B 9/00 |
| 0 684 037 A1 | 11/1995 | United Kingdom | A61K 7/32 |
| WO 92/00722 | 7/1990 | WIPO | |
| 9516432 | 6/1995 | WIPO | |
| WO 96/12467 | 9/1995 | WIPO | |
| WO 96/12468 | 9/1995 | WIPO | |
| WO 96/32918 | 3/1996 | WIPO | |

OTHER PUBLICATIONS

XP–002067076 Steffen Arctander: "Perfume and Flavor Chemicals" Apr. 1, 1982, Montclair, NJ, USA.
Chemical Abstract No. 1993:105355; Japan; Jun. 30, 1992.
Chemical Abstract No. 92–295410; Japan; Oct. 20, 1992.

*Primary Examiner*—Cecilia J. Tsang
*Assistant Examiner*—S. G. Marshall
*Attorney, Agent, or Firm*—Stephen T. Murphy

[57] ABSTRACT

The present invention relates to personal care and pharmaceutical compositions comprising an alcohol, a personal care polymer, and an alcohol-masking perfumery component. These compositions can be applied to the skin, hair, or mucosa. The alcohol-masking perfumery component substantially reduces both the alcohol odor or aroma and the stinging or burning sensation in the nose or throat due to the alcohol when the compositions are sprayed or atomized.

17 Claims, No Drawings

SPRAY COMPOSITIONS

TECHNICAL FIELD

The present invention relates to personal care and pharmaceutical compositions for use on the skin, hair, and mucosa. These compositions comprise an alcohol, a personal care polymer, and an alcohol-masking perfumery component The alcohol-masking perfumery component substantially reduces both the odor or aroma of alcohol and the stinging or burning sensation in the nose or throat due to the alcohol when the compositions are sprayed or atomized.

BACKGROUND OF THE INVENTION

Many products, such as personal care and pharmaceutical compositions that are used by spraying or atomizing, often contain high concentrations of alcohol (i.e. greater than about 60% alcohol by weight). These high-alcohol content compositions can create both an undesirable odor of alcohol and an undesirable stinging or burning sensation in the nose or throat when the composition is sprayed or atomized. As a result, both the alcohol odor and the alcohol sting can greatly decrease consumer acceptance and, consequently, use of the product.

In most cases the alcohol content is a vital component of the composition, because alcohol is an excellent solvent for facilitating the delivery of a wide variety of cosmetic and pharmaceutical actives, and because it readily evaporates after facilitating the delivery of active components. Many cosmetic and pharmaceutical products contain polymeric material which can provide benefits such as, rheological properties, aesthetic properties, delivery and substantivity of actives, skin or hair conditioning, hair styling, etc. Because many polymeric materials are alcohol soluble, decreasing the concentration of alcohol in such compositions is not desirable, and in some cases not feasible. Thus, high-alcohol content compositions having substantially reduced alcohol odor and alcohol sting are desired.

To achieve the desirable objectives discussed in the preceding paragraph, the proper physiological mechanisms of alcohol sense perception should be understood. Without being limited by theory, it is believed that alcohol affects two different physiological mechanisms. At lower concentrations the odor of alcohol is perceived through the sense of smell as being "sweet smelling." However, it is believed that at higher alcohol concentrations the alcohol reaches a threshold level and also causes a stinging or burning sensation in the nose or throat. The traditional approaches to masking the odor of alcohol have failed to account for these two differing mechanisms.

One traditional approach to overcoming the alcohol odor and alcohol sting is to simply add perfumes. This approach, however, merely results in compositions that smell like the perfume, but fail to reduce the alcohol sting. Thus, at higher alcohol concentrations, overpowering the sense of smell with perfumes fail to substantially reduce the alcohol sting. This ineffective approach results from the common misconception of equating the stinging or irritation of alcohol to the smell or odor of alcohol. The compositions of the present invention address both problems by substantially reducing both the alcohol odor and the alcohol sting.

It has been surprisingly found in the present invention that compositions comprising certain perfumery components substantially reduce both the alcohol odor and the alcohol sting, even from sprayed or atomized compositions having a high alcohol concentration (e.g. greater than about 60 by weight of the composition). Additionally, these perfumery components do not substantially interfere with the parent or signature fragrance of the compositions which may be ineffective in substantially masking or reducing the alcohol odor and sting. It is desireable to not interfere with the parent or signature fragrance of a composition because consumers may identify the signature fragrance with the product or because the signature fragrance may have the best consumer acceptance.

It is, therefore, an object of the present invention to provide personal care and pharmaceutical compositions having a high alcohol content (e.g., greater than about 60% by weight of the composition) and a personal care polymer which comprises an alcohol-masking perfumery component which substantially reduces both the odor of alcohol and the stinging sensation in the nose or throat when the compositions are sprayed or atomized.

It is another object of the present invention to substantially reduce both the odor and the stinging sensation of alcohol in high alcohol-content compositions (e.g., greater than about 60% by weight of the composition) without decreasing the alcohol content.

It is another object of the present invention to substantially reduce the stinging sensation of alcohol in high alcohol-content compositions while not significantly interfering with the parent or signature fragrance of the compositions.

It is another object of the present invention to increase consumer acceptance of high-alcohol content compositions which are used by spraying or atomizing the compositions.

These and other objects of this invention will become apparent in light of the following disclosure.

SUMMARY OF THE INVENTION

The present invention relates to compositions suitable for use on the skin, hair or mucosa, comprising:
- (a) from about 60% to about 99.9% by weight of said composition of alcohol,
- (b) from about 0.01% to about 20% by weight of said composition of a personal care polymer, and
- (c) from about 0.001% to about 0.3% by weight of said composition of a perfumery component which substantially masks or reduces both the odor and the stinging sensation of said alcohol in the nose or throat, wherein said composition is sprayed or atomized upon use.

A method of substantially masking or reducing both the odor and the stinging sensation in the nose or throat from an atomized alcohol containing composition, said method comprising the steps of:
- (1) preparing a composition comprising:
  - (a) from about 60% to about 99.9% by weight of said composition of alcohol,
  - (b) from about 0.01% to about 20% by weight of said composition of a personal care polymer, and
  - (c) from about 0.001% to about 0.3% by weight of said composition of a perfumery component which substantially masks or reduces both the odor and the stinging sensation of said alcohol in the nose or throat, and
- (2) atomizing or spraying said composition.

A method of substantially reducing trigeminal stimulation from an atomized alcohol containing composition, said method comprising the steps of:
- (1) preparing a composition comprising:
  - (a) from about 60% to about 99.9% by weight of said composition of alcohol, (b) from about 0.01% to about 20% by weight of said composition of a personal care polymer, and (c) from about 0.001% to about 0.3% by weight of said composition of a perfumery component which substantially reduces trigeminal stimulation, and (2) atomizing or spraying said composition.

The present invention also relates to methods of using these compositions.

All percentages and ratios used herein are by weight of the total composition and all measurements made are at 25° C. or room temperature, unless otherwise designated. All weight percentages, unless indicated, are on an actives weight basis. The invention hereof can comprise, consist of, or consist essentially of, the essential, as well as, the optional ingredients and additional components described herein.

DETAILED DESCRIPTION OF THE INVENTION

The compositions of the present invention are suitable for topical application to the skin, hair, or mucosa. These compositions comprise alcohol, a personal care polymer, and a perfumery component which substantially masks or reduces the odor or aroma of alcohol and the stinging or burning sensation of alcohol in the nose or throat when the compositions are used by spraying or atomizing.

The term "alcohol-masking," as used herein, describes the effect of a perfumery component to substantially mask or reduce both the odor or aroma of the alcohol and the stinging or burning sensation of alcohol in the nose or throat which results from the spraying or atomizing of a high-alcohol content composition.

The term "substantially reduces or masks," as used herein, means that the perfumery component mitigates both the odor or aroma and the stinging or burning sensation in the nose or throat. This designation relates to an alcohol-masking potential value of greater than about 2.8, as described further in this patent.

The term "spraying or atomizing", as used herein, means to reduce a composition into minute particles, or into a vapor, or into a finely divided liquefied dispersion.

The term "high-alcohol content compositions," as used herein, means compositions that comprise greater than about 60% alcohol by weight of the composition.

The term "stinging sensation," as used herein, means the burning or stinging sensation in the nose or throat when a high-alcohol content composition is sprayed or atomized. The stinging sensation produced by alcohol is also described as the alcohol sting.

The term "alcohol odor," as used herein, means the odor, aroma, scent, or smell of alcohol.

SPRAY COMPOSITIONS

The compositions of the present invention are in the form of products which are sprayed or atomized. The products can be delivered from non-aerosol mechanical pump spray devices or from pressurized aerosol canisters using a propellant or from any other mechanism or method of dispersing compositions for application to the skin, hair, or mucosa. A wide range of mechanical pump spray devices and aerosol canister systems are well known to those of ordinary skill in the art. Similarly, a wide range of propellant materials are well known to those skilled in the art. Nonlimiting examples of such propellants include, but are not limited to chlorinated, fluorinated, and chlorofluorinated lower molecular weight hydrocarbons; nitrous oxide; carbon dioxide; butane; isobutane; propane; and mixtures thereof. The propellants are used at a level sufficient to expel the contents of the container.

ALCOHOL

The compositions of the present invention comprise alcohol. The term "alcohol," as used herein, means alcohols selected from the group consisting of ethanol iso-propanol, n-propanol and mixtures thereof, more preferably ethanol, iso-propanol and mixtures thereof, most preferably ethanol. The compositions of the present invention comprise from about 60% to about 99.9%, preferably from about 65% to about 95%, and more preferably from about 70% to about 85%, by weight of the composition of alcohol.

Any grade of alcohol that is cosmetically or pharmaceutically acceptable can be used in the compositions of the present invention. Also, standard cosmetically- or pharmaceutically-acceptable denaturing agents can be used with the ethanol.

PERSONAL CARE POLYMER

The compositions of the present invention comprise a personal care polymer. The compositions of the present invention comprise from about 0.01% to about 20%, preferably from about 0.05% to about 15%, and more preferably from about 0.1% to about 10% by weight of the composition of a personal care polymer. The term "personal care polymer," as used herein, is defined as a natural or synthetic polymer which is substantially soluble or dispersible in alcohol comprising compositions and which is cosmetically or pharmaceutically acceptable for application to the skin, hair, and mucosa. The term "substantially soluble or dispersible," as used herein, means that the polymer has a solubility or dispersibility in alcohol (as defined herein) of at least about 0.01% by weight at 25° C.

Useful personal care polymers are disclosed in one or more of the following patents: U.S. Pat No. 4,234,464, to Morshauser, issued Nov. 18, 1980; U.S. Pat No. 4,061,602, to Oberstar et al., issued Dec. 6, 1977; U.S. Pat No. 4,472,297, to Bolich et al., issued Sep. 18, 1984; U.S. Pat No. 4,491,539, to Hoskins et al., issued Jan. 1, 1985; U.S. Pat No. 4,540,507, to Grollier, issued Sep. 10, 1985; U.S. Pat No. 4,673,525, to Small et al., issued Jun. 16, 1987; U.S. Pat No. 5,106,609, to Bolich Jr. et al., issued Apr. 21, 1992; and U.S. Pat No. 5,494,533, to Woodin Jr. et al., issued Feb. 27, 1996. All of the above patents are incorporated herein by reference, especially for their basic personal care product and polymer disclosures.

Anionic, nonionic, amphoteric, and cationic polymers can all be useful in the compositions of the present invention if the requirements of solubility are met. The compositions of the present invention comprise a polymer selected from the group consisting of gums, resins, proteins, polysaccharides, carboxylic acid polymers, polyacrylates, polyacrylamides, vinyl ether/maleic anhydride copolymers, poly (N-vinylpyrolidones), silicones, silicone copolymers, and mixtures thereof. The following are non-limiting examples of useful polymers in the compositions of the present invention.

Gums and Resins: Polymers useful herein include materials generally referred to by those skilled in the art as gums and resins which are primarily derived from natural sources. Nonlimiting examples of these gums include materials selected from the group consisting of acacia, agar, algin, alginic acid, ammonium alginate, amylopectin, bentonite, calcium alginate, calcium carrageenan, carnitine, carrageenan, corn starch, dextrin gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, magnesium aluminum silicate, magnesium silicate, magnesium trisilicate, montmorillonite, natto gum, potassium alginate, potassium carrageenan, propylene glycol alginate, sclerotium gum, sodium carboyxmethyl dextran, sodium carrageenan, sodium polyacrylate starch, sodium silicoaluminate, starch/acrylates/acrylamide copolymer, tragacanth gum, xanthan gum, and mixtures thereof.

The polymers derived primarily from natural sources, discussed above, can also be copolymerized with synthetic monomers. Some of these desirable polymers are bulky amine polymers having the following generalized formula in which the backbone is represented by "POLYMER" and having the indicated non-labile cationic functional group:

(I) $(POLYMER)-(CR^1H-CR^2R^3-NR^4R^5R^6)_x$
wherein $R^1$–$R^3$ is H or any other substituent and $R^4$, $R^5$ and $R^6$ combine with N to form an amine with less odor impact than trimethylamine, preferably at least one of $R^4$, $R^5$ and $R^6$ is alkyl having a chain length of from about 2 to about 24 carbon atoms, or an alkoxyallyl group containing from about 2 to about 12 carbon atoms.

Some examples of preferred bulky amine polymers are cationic guar gums having the following structures, wherein "guar" represents the guar gum backbone:

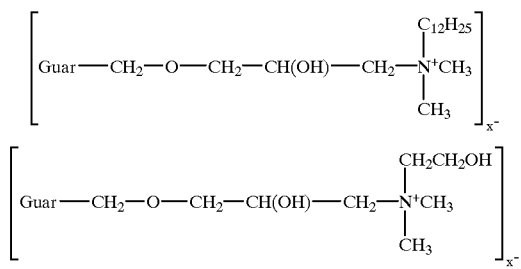

An example of a bulky amine hydroxyethyl cellulose (HEC) polymer is:

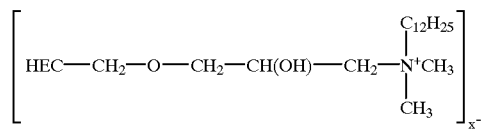

The "x" in the above formulae is typically selected to provide a degree of substitution of from about 0.5 to about 4, preferably from about 1 to about 2.5. These "bulky amine" groups have no odor problem and also have improved skin conditioning benefits.

Some preferred cationic guars (galactomannans) are disclosed in U.S. Pat No. 4,758,282, Stober et al., issued Jul. 19, 1988, incorporated herein by reference. The cationic guar gum polymers disclosed in U.S. Pat Nos. 4,946,618 to J. R Knochel and P. E. Vest, issued Aug. 7, 1990, incorporated by reference herein, are suitable, especially when the cationic groups are substituted with bulky amine groups.

Polysaccharides: A wide variety of polysaccharides are useful herein. By "polysaccharides" are meant polymers containing a backbone of repeating sugar (i.e. carbohydrate) units. Nonlimiting examples of polysaccharide polymers include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10–C30 straight chain or branched chain alkyl group through an ether linkage. Typically these polymers are ethers of C10–C30 straight or branched chain alcohols with hydroxyalkylcelluloses. Examples of allyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl linoleyl, linolenyl, ricinoleyl behenyl, and mixtures thereof.

Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation. Other useful polysaccharides include scleroglucans comprising linked glucose units, a commercially available example of which is Clearogel™ CS11 from Michel Mercier Products Inc. (Mountainside, N.J.). Still other useful examples include: hydroxyethyl cellulose (e.g., Natrosol 150MXR, Natrosol 250HR, etc.); and cationic cellulose polymers (e.g., Union Carbide's JR400).

Copolymers of saccharides and synthetic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Xanthan gum, e.g., Keltrol T, (molecular weight about 2,000,000) is also a suitable polymer. Also included are hydroxymethyl, hydroxyethyl and hydroxypropyl derivatives of the above sugars.

Proteins: A wide variety of proteins are useful herein. By "proteins" are meant polymers containing a backbone of repeating amino acids units. Nonlimiting examples of protein polymers include those selected from the group consisting of ethyl ester of hydrolyzed animal protein, hydrolyzed collagen, hydrolyzed fibronectin, oat protein, lauryl hydrolyzed collagen, hydrolyzed conchiorin protein, hydrolyzed corn protein, hydrolyzed spinal protein, ammonium hydrolyzed collagen, hydrolyzed milk protein, TEA-abietoyl hydrolyzed collagen, potassium abietoyl hydrolyzed collagen, isostearoyl hydrolyzed collagen, TEA-isostearoyl hydrolyzed collagen, potassium lauroyl hydrolyzed collagen, TEA-lauroyl hydrolyzed collagen, myristoyl hydrolyzed collagen, sodium myristoyl hydrolyzed collagen, TEA-myristoyl hydrolized collegen, oleoyl hydrolyzed collagen, ThA-oleoyl hydrolyzed collagen, potassium oleoyl hydrolyzed collagen, palmitoyl hydrolyzed collagen, potassium stearoyl hydrolyzed collagen, palmitoyl hydrolyzed collagen, potassium stearoyl hydrolyzed collagen, TEA-undecylenoyl hydrolyzed collagen, potassium undecylenoyl hydrolyzed collagen, zinc hydrolyzed collagen, sodium lauroyl hydrolyzed collagen, sodium/TEA-lauroyl collagen amino acids, potassium myristoyl hydrolyzed collagen, sodium oleoyl hydrolyzed collagen, sodium stearoyl hydrolyzed collagen, casein, hydrolyzed casein, hydrolyzed pea protein, hydrolyzed potato protein, hydrolyzed rice bran protein, hydrolyzed rice protein, hydrolyzed serum protein, soy protein, hydrolyzed vegetable protein, wheat protein hydrolyzed wheat protein, hydrolyzed yeast protein, what germ protein, whey protein, and mixtures thereof.

Carboxylic Acid Polymers: Carboxylic acid polymers are also useful herein. Carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e. a $C_{1-4}$) acrylate ester monomer or derivative thereof (e.g., wherein the acrylic acid portion of the ester has substituents on the two and three carbon positions independently selected from the group consisting of $C_{1-4}$ allyl, —CN, —COOH, and mixtures thereof), and mixtures thereof, and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof with the $C_{1-4}$ alcohol acrylate esters, $C_{1-4}$ alcohol methacrylate esters, and mixtures thereof being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also, *CTFA International Cosmetic Ingredient Dictionary,* fourth edition, 1991, pp. 12 and 80; which are also incorporated herein by reference in their entirety.

Examples of commercially available homopolymers of the first type useful herein include the carbomers, which are homopolymers of acrylic acid crosslinked with allyl ethers of sucrose or pentaerytritol. The carbomers are available as the Carbopol® 900 series from B. F. Goodrich. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commercially available as Carbopol® 1342, Pemulen TR-1, and Pemulen TR-2, from B. F. Goodrich. In other words, examples of carboxylic acid polymer thickeners useful herein are those selected from the group consisting of carbomers, acrylates/C10–C30 allyl acrylate crosspolymers, and mixtures thereof.

Polyacrylate Polymers: The polyacrylate polymers which are useful herein include both cationic and nonionic polymers, with the cationics being generally preferred. Examples of useful polyacrylates include crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoallyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon-carbon double bond or other such polymerizable functional group, I is an integer of 0 or greater, m is an integer of 0 or greater, n is an integer of 0 or greater, but where either 1 or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, and most preferably $C_1$–$C_2$. When quaternized, the polymers are preferably quaternized with short chain allyls, i.e., $C_1$–$C_8$, preferably $C_1$–$C_5$, more preferably $C_1$–$C_3$, and most preferably $C_1$–$C_2$. The acid addition salts refer to polymers having protonated amino groups. Acid addition salts can be performed through the use of halogen (e.g. chloride), acetic, phosphoric, nitric, citric, or other acids.

These $(A)_1(B)_m(C)_n$ polymers also comprise a crosslinking agent, which is most typically a material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaeythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifing effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects in water or other aqueous carriers of the compositions hereof. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l(B)_m(C)_n$ wherein 1 is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare® SC92 from Allied Colloids Ltd (Norfolk, Va.). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which 1 is also zero. In this instance the polymer is essentially a homopolymer of a dialkylaminoalkyl methacrlyate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein 1 is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd., (Norfolk, Va.) under the trademark Salcare® SC95. This polymer has recently been given the CTFA designation "Polyquaternium 37 (and) Mineral Oil (and) PPG-1 Trideceth-6".

Polyacrylamide Polymers: Also useful herein are polyacrylamide polymers, especially non-ionic polyacrylamide polymers including substituted branched or unbranched polymers. These polymers can be formed from a variety of monomers including acrylamide and methacrylamide which are unsubstituted or substituted with one or two allyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl ethyl or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Vinyl Ether/Maleic Anhydride Copolymers: Other polymers useful herein include copolymers of allyl vinyl ethers and maleic anhydride, preferably crosslinked polymers or this type. In these copolymers the vinyl ethers are represented by the formula R—O—CH=CH$_2$ wherein R is a C1–C6 alkyl group, preferably R is methyl. Preferred crosslinking agents are C4–C20 dienes, preferably C6 to C16 dienes, and most preferably C8 to C12 dienes. A particularly preferred copolymer is one formed from methyl vinyl ether and maleic anhydride wherein the copolymer has been crosslinked with decadiene, and wherein the polymer when diluted as a 0.5% aqueous solution at pH 7 at 25° C. has a viscosity of 50,000–70,000 cps when measured using a Brookfield RTV viscometer, spindle #7 at 10 rpm. This copolymer has the CTFA designation PVM/MA decadiene crosspolymer and is commercially available as Stabileze™ 06 from International Specialty Products (Wayne N.J.).

Poly(N-vinylpyrrolidones): Polyvinyl(N-pyrrolidones) useful herein include those described in U.S. Pat. No. 5,139,770, to Shih et al, issued Aug. 18, 1992, and U.S. Pat. No. 5,073,614, to Shih et al., issued Dec. 17, 1991, both patents of which are incorporated by reference herein in their entirety. These polymers are preferably crosslinked and typically contain from about 0.25% to about 1% by weight of a crosslinking agent selected from the group consisting of divinyl ethers and diallyl ethers of terminal diols containing from about 2 to about 12 carbon atoms, divinyl ethers and diallyl ethers of polyethylene glycols containing from about 2 to about 600 units, dienes having from about 6 to about 20 carbon atoms, divinyl benzene, vinyl and allyl ethers of pentaerythritol, and the like. Typically, these polymers have a viscosity from about 25,000 cps to about 40,000 cps when measured as a 5% aqueous solution at 25° C. using a Brookfield RVT viscometer with Spindle #6 at 10 rpm. Commercially available examples of these polymers include ACP-1120, ACP-1179, and ACP-1180, available from International Specialty Products (Wayne, N.J.).

Silicones: Other polymers useful in the compositions of the present invention are silicone polymer materials. Although silicone fluids are useful in the present compositions, preferred silicone polymers are rigid silicone polymers. Such materials are described in U.S. Pat. No. 4,902,499, Bolich et al., issued Feb. 20, 1990, U.S. Pat No. 4,906,459, Bolich et al., issued Mar. 6, 1990, U.S. Pat No. 5,106,609, Bolich, Jr. et. al., issued Apr. 21, 1992, EP 412704 published Feb. 7, 1991, and EP 412707, published Feb. 13, 1991, all five being incorporated by reference herein in their entirety.

Some examples of such materials include, but are not limited to, filer reinforced polydimethylsiloxane gums including those having end groups such as hydroxyl; cross linked siloxanes, such as organic substituted silicone elastomers, organic substituted siloxane gums, including those having end groups such as hydroxyl; resin reinforced siloxanes; and cross linked siloxane polymers.

The rigid silicone polymers useful in the present invention have complex viscosities of at least $2 \times 10^5$ poise (), preferably about $1 \times 10^7$ poise, where complex viscosity is measured by subjecting a sample to oscillatory shear at a fixed frequency of 0.1 rad/sec at 25° C. using a Rheometric Fluids Spectrometer.RTM. measuring films having a thickness of about 1 millimeter. The resulting viscous and elastic force responses are combined to determine the complex modulus which is divided by the imposed frequency to compute the complex viscosity.

The siloxane gums may also be filler reinforced to provide additional rigidity. Silica is the preferred filler. Generally such reinforced gums comprise up to about 15–20 wt % silica.

Silicone elastomers useful in the compositions of the present invention are the materials described in U.S. Pat No. 4,221,688, Johnson et al., issued Sep. 9, 1980, incorporated herein by reference. The actual material described in the patent and what can be put into the present compositions is an aqueous emulsion which dries to form an elastomer upon removal of the water.

Silicone resins useful in the present compositions are silicone polymers with a high degree of crosslinking introduced through the use of trifunctional and tetrafunctional silanes. Typical silanes used in the manufacture of resins are monomethyl, dimethyl, monophenyl, diphenyl, methylphenyl monovinyl, and methylvinyl chlorosilanes, together with tetrachlorosilane. A preferred resin is one offered by General Electric as GE SR545. This resin is provided as a solution in toluene which is stripped prior to the resin's use.

Other rigid silicone polymers of use herein are those siloxanes which have been sparingly crosslinked but are still soluble in solvents such as cyclomethicone. Precursors for the rigid material can be nay high molecular weight polydimethyl siloxanes, polydimethyl siloxanes containing vinyl groups and other siloxanes. Methods of crosslinking include heat curing with organic peroxides such a dibenzoyl peroxide and di-t-butyl peroxide, heat vulcanization with sulfur, and high-energy radiation.

Generally, the silicone gum, if used in the present compositions, is dissolved in a volatile carrier, or mixtures thereof, prior to incorporation into the hair care compositions. Preferably, the volatile carrier is present in the hair care composition at from about 0.1 wt % to about 20 wt % of the hair care composition. These materials can comprise the volatile liquid hydrocarbon or silicone fluids described supra.

Preferably the rigid silicone polymer and carrier comprises from about 0.1 wt. % to about 2.5 wt. % of a polydimethylsiloxane gum; from about 0.02 wt % to about 0.7 wt % of fumed silica, and from about 0.4 wt. % to about 18 wt. % of a volatile silicone carrier.

Silicone Copolymers: Also useful in the compositions of the present invention are silicone copolymers. The following examples are nonlimiting as the possible combinations of silicone copolymers are limitless.

Highly preferred polymers for use in the compositions of the present invention are hair holding/styling polymers. Highly preferred examples of such materials are the silicone-containing copolymers as described in the following patent applications: Ser. No. 390,559, Torgerson, Bolich and Garbe, filed Aug. 7, 1989, now abandoned, which is the parent application of U.S. Ser. No. 07/505,760 filed Apr. 6, 1990, now abandoned, which is the parent application of U.S. Ser. No. 07/758,320, filed Aug. 27, 1991; and Ser. No. 390,568, Bolich and Torgerson, filed Aug. 7, 1989, now abandoned, which is the parent application of U.S. Ser. No. 07/505,755, filed Apr. 6, 1990, now abandoned, which is the parent application of U.S. Ser. No. 07/758,319, filed Aug. 27, 1991; both of which are incorporated by reference herein. Such polymers should have a weight average molecular weight of from about 10,000 to about 1,000,000 and preferably, have a Tg of at least about −20° C. As used herein, the abbreviation "Tg" refers to the glass transition temperature of the non-silicone backbone, and the abbreviation "Tm" refers to the crystalline melting point of the non-silicone backbone, if such a transition exists for a given polymer.

Preferred polymers comprise a vinyl polymeric backbone having a Tg or a Tm above about—20° C. and, grafted to the backbone, a polydimethylsiloxane macromer having a weight average molecular weight of from about 1,000 to about 50,000, preferably from about 5,000 to about 40,000, most preferably from about 10,000 to about 20,000. The polymer is such that when it is formulated into the finished hair care composition, when dried, the polymer phase separates into a discontinuous phase which includes the polydimethylsiloxane macromer and a continuous phase which includes the backbone. It is believed that this phase separation property provides a specific orientation of the polymer on hair which results in the desired hair conditioning and setting benefits.

In its broadest aspect, the copolymers utilized in the present application comprise C monomers together with monomers selected from the group consisting of A monomers, B monomers, and mixtures thereof. These copolymers contain at least A or B monomers together with C monomers, and preferred copolymers contain A, B and C monomers.

Examples of useful copolymers and how they are made are described in detail in U.S. Pat No. 4,693,935, Mazurek, issued Sep. 15, 1987, and U.S. Pat. No. 4,728,571, Clemens et al, issued Mar. 1, 1988, both of which are incorporated herein by reference. These copolymers are comprised of monomers A, C and, optionally, B, which are defined as follows. A, when used, is at least one free radically polymerizable vinyl monomer or monomers. B, when used, comprises at least one reinforcing monomer copolymerizable with A and is selected from the group consisting of polar monomers and macromers having a Tg or a Tm above about −20° C. When used, B may be up to about 98 wt. %, preferably up to about 80 wt %, more preferably up to about 20 wt. %, of the total monomers in the copolymer. Monomer C comprises from about 0.01 wt % to bout 50.0 wt. %, of the total monomers in the copolymer.

Representative examples of A monomers are acrylic or methacrylic acid esters of $C_1$–$C_{18}$ alcohols, such as methanol, ethanol, 1-propanol, 2-propanol, 1-butanol, 2-methyl-1-propanol, 11-pentanol, 2-pentanol, 3-pentanol, 2-methyl-11-butanol, 1-methyl-l-butanol 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2octanol, 6-methyl-11-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; vinyl acetate; vinyl chloride; vinylidene chloride; acrylonitrile; alpha-methylstyrene; t-butylstyrene; butadiene; cyclohexadiene; ethylene; propylene; vinyl toluene; and mixtures thereof. Preferred A monomers include n-butyl methacrylate, isobutyl methacrylate, 2-ethylhexyl methacrylate, methyl methacrylate, t-butylacrylate, t-butylmethacrylate, and mixtures thereof.

Representative examples of B monomers include acrylic acid, methacrylic acid, N,N-dimethylacrylamide, dimethylaminoethyl methacrylate, quaternized dimethylaminoethyl methacrylate, methacrylonitrile, polystyrene macromer, methacrylamide, maleic anhydride and its half esters, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, acylactones, 2-ethyl-21-oxazoline, vinyl pyridine, vinyl imidazole, other polar vinyl heterocyclics, styrene sulfonate, and mixtures thereof. Preferred B monomers include acrylic acid, N,N-dimethylacrylamide, dimethylaminoethyl methacrylate, quaternized dimethylaminoethyl methacrylate, vinyl pyrrolidone, and mixtures thereof.

The C monomer has the general formula:

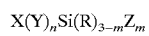

wherein X is a vinyl group copolymerizable with the A and B monomers; Y is a divalent linking group; R is a hydrogen, lower allyl, aryl or alkoxy; Z is a monovalent siloxane polymeric moiety having a number average molecular weight of at least about 500, is essentially unreactive under copolymerization conditions and is pendant from the vinyl polymeric backbone, described above; n is 0 or 1; and m is an integer from 1 to 3. C has a weight average molecular weight of from about 1,000 to about 50,000, preferably from about 5,000 to bout 40,000, most preferably from about 10,000 to about 20,000. preferably, the C monomer has a formula selected from the following group:

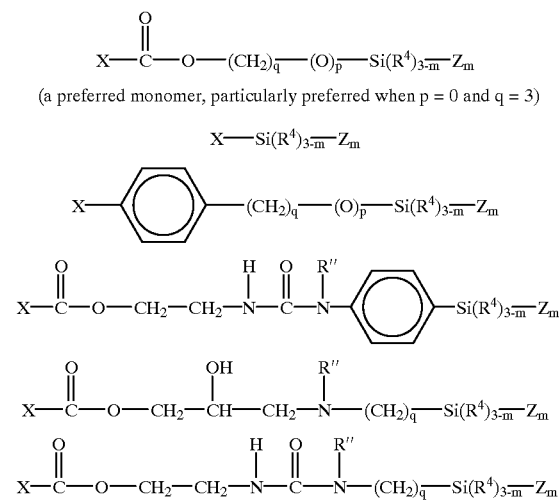

In those structures, m is 1, 2 or 3 (preferably m=1); p is 0 or 1; R" is alkyl or hydrogen; q is an integer from 2 to 6; s is an integer from 0 to 2; X is

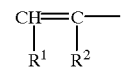

$R^1$ is hydrogen or —COOH (preferably $R^1$ is hydrogen); $R^2$ is hydrogen, methyl or —$CH_2$ COOH (preferably $R^2$ is methyl); Z is

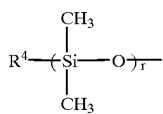

$R^4$ is allyl alkoxy, alkylamino, aryl, or hydroxyl (preferably $R^4$ is alkyl); and r is an integer from about 5 to about 700 (preferably r is about 250).

The preferred polymers useful in the present invention generally comprise from 0 wt. % to about 98 wt. % (preferably from about 5 wt. % to about 98 wt. %, more preferably from about 50 wt. % to about 90 wt. %) of monomer A, from 0 wt. % to about 98 wt. % (preferably from about 7.5 wt % to about 80 wt. %) of monomer B, and from about 0.1 wt. % to about 50 wt. % (preferably from about 0.5 wt. % to about 40 wt. %, most preferably from about 2 wt % to about 25 wt. %) of monomer C. The combination of the A and B monomers preferably comprises from about 50.0 wt. % to bout 99.9 wt. % (more preferably about 60 wt. % to about 99 wt. %, most preferably from about 75 wt. % to about 95 wt. %) of the polymer. The composition of any particular copolymer will help determine its formulational properties. For example, polymers which are soluble in an aqueous formulation preferably have the composition: from 0 wt. % to about 70 wt. % (preferably from about 5 wt. % to about 70 wt. %) monomer A, from about 30 wt. % to about 98 wt. % (preferably from about 3 wt. % to about 80 wt. %) monomer B, and from about 1 wt. % to about 40 wt. % monomer C. Polymers which are dispersible have the preferred composition: from 0 wt.% to bout 70 wt. % (more preferably from about 5 wt. % to bout 70 wt. %) monomer A, from about 20 wt. % to about 80 wt. % (more preferably from about 20 wt. % to bout 60 wt. %) monomer B, and from about 1 wt. % to about 40 wt. % monomer C.

Particularly preferred polymers for use in the present invention include the following (the weight percents below refer to the amount of reactants added in the polymerization reaction, not necessarily the amount in the finished polymer): (I) acrylic acid/n-butylmethacrylate/polydimethylsiloxane (PDMS) macromer-20,000 molecular weight (10.70.20 w/w/w); (II) N,N-dimethylacrylamide/isobutyl methacrylate/PDMS macromer-20,000 molecular weight (20/60/20 w/w/w); (III) dimethylaminoethyl methacrylate/isobutyl methacrylate/2-ethylhexyl-methacrylate/PDMS macromer-20,000 molecular weight (25/40/15/20 w/w/w/w); (IV) dimethylacrylamide/PDSM macromer-20,000 molecular weight (80/20 w/w); (V) t-butylacrylate/t-butylmethacrylate/PDMS macromer-10,000 molecular weight (56/24/20 w/w/w); (VI) t-butylacrylate/PDMS macromer-10,000 molecular weight (80/20 w/w); (VII) t-butylacrylate/N,N dimethylacrylamide/PDMS macromer-10,000 molecular weight (70/10/20 w/w/w); (VIII) t-butylacrylate/acrylic acid/PDMS macromer-10,000 molecular weight (75/5/20 w/w/w).

The particle size of the copolymer material of the present compositions may have some effect on performance in product. This, of course, will vary from copolymer to copolymer and from product to product.

The copolymers are preferably combined with a solvent for the copolymer prior to combination with the vehicle systems of the present invention.

The solvent selected must be able to dissolve or disperse the particular silicone copolymer being used. The nature and proportion of B monomer in the copolymer largely determines its polarity and solubility characteristics. The silicone copolymers can be designed, by appropriate combination of monomers, for formulation with a wide range of solvents. Suitable solvents for use in the present invention include, but are not limited to, water, lower alcohols (such as ethanol isopropanol), hydroalcoholic mixtures, hydrocarbons (such as isobutane, hexane, decene, acetone), hydrogenated hydrocarbons (such as Freon), linalool, hydrocarbon esters (such as ethyl acetate, dibutyl phthalate), volatile silicon derivatives, especially siloxanes (such as phenyl pentamethyl disiloxane, phenethyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof. Preferred solvents include water, ethanol volatile silicone derivatives, and mixtures thereof.

Preferred polymers for use in the compositions of the present invention are selected from the group consisting of xanthan gum; guar gum; myristoyl hydrolized collagen; polyacrylic acids; acrylates/C10–C30 alkyl acrylate crosspolymers; homopolymers of acrylic acid crosslinked with an allyl ether of pentaerylthriotol, an allyl ether of sucrose, or an allyl ether of propylene (tradename Carbomer); polyacrylic acids; vinyl acetate/crotonates copolymer; vinyl acetate/crotonates/vinyl neadecanoate copolymers; octylacrylamide/acrylates/butylaminoethyl methacrylate copolymers; polyvinylpyrrolidone/vinyl acetate copolymers; polyquaternium 10 through 30; PVM/MA copolymers; PVM/VA decadiene crosspolymers; butyl ester of PVM/MA copolymers; ethyl ester of PVM/MA copolymers; isopropyl ester of PVM/MA copolymers; polyvinyl methyl ether polymers; stearylvinyl ether/MA copolymers; acrylates/dimethicone crosspolymers, and mixtures thereof.

ALCOHOL-MASKING PERFUMERY COMPONENT

The compositions of the present invention comprise an alcohol-masking perfumery component. The compositions comprise from about 0.001% to about 0.3%, preferably from about 0.01% to about 0.25%, more preferably from about 0.05% to about 0.2%, and most preferably from about 0.05% to about 0.15% by weight of the composition of the alcohol-masking perfumery component. The alcohol-masking perfumery component comprises one or more perfumery compounds which substantially reduces both the odor or aroma of alcohol and the stinging or burning sensation of alcohol in the nose or throat when the compositions of the present invention are sprayed or atomized.

The alcohol-masking perfumery component is selected from the group consisting of C2–C20 aldehydes, C5–C15 esters, C4–C15 alcohols, C4–C20 ethers, C3–C15 ketones, and mixtures thereof. The alcohol-masking perfumery component is preferably selected from the group consisting of C7–C15 aldehydes, C8–C13, C4–C10 alcohols, C14–C17 ethers, C9–C12 ketones, and mixtures thereof.

Examples of C2–C20 aldehydes useful in the compositions of the present invention are selected from the group consisting of beta-methyl-3-(1-methylethyl) Benzenepropanal, Phenoxy Acetaldehyde, 1- nonanal, 2-Methyl Undecanal Methyl Nonyl Acetaldehyde, 3,7-Dimethyl-2-Methylene-6-Octenal, Phenoxy Acetaldehyde, 3-Cyclohexene-1-carbox-aldehyde,4-(4-hydroxy 4 Methyl Pentyl), Phenoxy Acetaldehyde, alpha-n-hexyl cinnamic Aldehyde, 2-Norpinene-2-Propion-aldehyde,6,6-Dimethyl, 3-Cyclohexene-1-Carbox-Aldehyde, 1-Methyl-4-(4-Methyl-3-Penenyl), 10-Undecenal, 3-Cyclohexene-1-carbox-aldehyde,4-(4-hydroxy-4-methyl pentyl), 4,7-

Methyanoindan-1-Carboxaldehyde, hexahydro, Benzaldehyde, 2,6-Dimethyl-5-hepten-1-al, 2-Methyl-3-(4-isopropylphenyl)propanal, cis-4-decen-1-al, cis-7-decen-1-al, cis6-nonen-1-al, Undecanal, Para-ethyl-alpha,alpha dimenthyl Hydrocinnamaldehyde, butyl cinnamic Aldehyde, 2-methyl-3,-(4tert-butylphynyl) Propanal, 4-methoxy Benzaldehyde, 1-Decanal, and mixures thereof.

Examples of C5–C15 esters useful in the compositions of the present invention are selected from the group consisting of Benzyl Ortho hydroxy benzoate, Phenyl Ortho Hydroxy Benzoate, 2-Buten-1-ol,3-Methyl:Acetate, 2-Propenyl-3-cyclohexylpropanoate, Allyl Hexanoate, 9-Hexadecenolide, Hexyl Salicylate, Methyl 2,4-decadienoate, Methyl 3-nonenoate, 9-Decen-1-yl acetate, ethyl-2-Methyl 3,4-Pentadienoate, cis-3-hexenyl Salicylate, and mixtures thereof.

Examples of C4–C15 alcohols useful in the present invention are 2,6-Nonadien-1-ol, Beta Gamma Hexenol, 3,7-Dimethyl-2,6-octadien-1-ol, 2,4-dimethyl-3-cyclohexene-1-Methanol, 1-Pentanol,3-methyl-5,5-phenyl, 2-phenyl ethyl Alcohol, 9-Decen-1-ol, 2-Methyl-3-phenylpropan-2-ol, 4-Methyl-3-decen-5-ol, and mixtures thereof.

Examples of C4–C20 ethers useful in the present invention are selected from the group consisting of napth(2,1-b)furan,decodecahydro-3a,6,6,9a-tetramethyl, 2-ethyl Furan, Hydrocinnamaldehyde, alpha-methyl-3,4-(methylenedioxy), 2-pentyl Furan, 2-(6-Methyl-8-(1-methylethyl) bicuclo<2.2.2.>oct-5-ene-2-(or3)yl-1, 3dioxolane, and mixtures thereof.

Examples of C3–C15 ketones useful in the present invention are selected from the group consisting of 2 hexyl cyclopentanone, Oxacycloheptadean-2-one, Gamma—Undecalactone, 3-Methyl-5-propyl-2-cyclohexen-1-one, 4-Nonanolide, Ethyl amyl ketone, 3-hepten-2-one, Methyl dihydrojasmonate, 3-decen-2-one, Geranyl Cyclopentanone, Dihydro alpha Ionone, 4-(2,6,6-Trimethyl-2-cyclohexen-1-yl)-3-methyl-3-butene-2-one, and mixtures thereof.

Preferred alcohol-masking perfumery compounds for use in the compositions are selected from the group consisting of beta-methyl-3-(1-methylethyl) Benzenepropanal, cis-4Decen-1-al, cis-7-Decen-1-al, cis-6-Nonen-1-al, Undecanal, Para-ethyl-alpha,alpha dimenthyl Hydrocinnamaldehyde, butyl cinnamic Aldehyde, 2-methyl-3,-(4-tert-butylphynyl) Propanal, 4-methoxy Benzaldehyde, 1-Decanal, 2 hexyl cyclopentanone, ethyl-2-Methyl 3,4-Pentadienoate, cis-3-hexenyl Salicylate, 2,6-Nonadien-1-ol, Napth(2,1-b)Furan,decodecahydro-3a,6,6,9a-tetramethyl, and mixtures thereof.

THE ALCOHOL-MASKING POTENTIAL TEST

The perfumery component of the present invention has an alcohol-masking potential grade of about 2.8 or greater, preferably about 3.0 or greater, more preferably about 3.2 or greater. The alcohol-masking potential test is used to determine the effectiveness of a perfumery component in substantially reducing both the alcohol odor or aroma and the alcohol sting or burning sensation of alcohol in the nose or throat. A blind, randomized evaluation is conducted with 9–10 panelists who are specially trained to discern scents.

A positive control and a negative control are used in the alcohol-masking potential test. The negative control comprises 74 wt. % specially denatured alcohol (denatured with Denatonium Benzoate 0.001% v/v & t-Butyl Alcohol 0.1% v/v); 4 wt. % personal care polymer, 17.6 wt. % water (USP Purified); 0.1 wt. % alcohol-masking perfumery component; and 4.3 wt. % optional ingredients. This negative control is assigned an alcohol-masking potential grade of 1. The positive control comprise 75% by weight of the composition of water and 25% by weight of the composition of ethanol. This positive control is assigned an alcohol-masking potential grade of 5. The 1 through 5 scale is explained below in the table.

The instructions given to the panelists are as follows:

1. Spray 2–3 pumps of the "Negative Control," identified as a "1", for Alcohol Coverage on the 5-point scale, wave in air, and familiarize yourself with this Base Line Control Product.
2. Spray 2–3 pumps of each "Unknown" sample into the 7 oz cup, wave in air for approximately 2 seconds, then evaluate versus the identified Negative Control. Evaluation should be based on the alcohol-masking potential grade (below) scale, which corresponds to how well the alcohol-masking material covers the alcohol odor and scent and the alcohol burning and stinging to the nose and throat.
3. Spray the sample again, if an additional evaluation is required. Take breaks between samples, and use tissues as necessary.

| Technical Grading Scale for the Detection of Alcohol Odor and Nasal Stinging & Burning | |
|---|---|
| 5 NO ALCOHOL ODOR NO NASAL STINGING OR BURNING | Unable to detect any Alcohol odor. No Nasal Stinging and/or Burning occurs. The only Odor detected is either a neutral, virtually odorless or non-descript odor, or a completely fragranced odor. |
| 4 SLIGHT ALCOHOL ODOR SLIGHT STINGING & BURNING | Able to detect a Slight Amount of Alcohol Odor with a Slight amount of nasal Stinging and/or Burning. Odor is essentially odorless/non-descript or essentially all fragrance with minimal Alcohol odor. Sample has minimal nasal Stinging and/or Burning. |
| 3 MODERATE ALCOHOL ODOR MODERATE STINGING & BURNING | Able to detect a Moderate Amount of Alcohol Odor, as well as, experiencing a Moderate Amount of Nasal Stinging and or Burning. The Alcohol impact is equal to the fragrance and/or neutral odor. |
| 2 SIGNIFICANT ALCOHOL ODOR SIGNIFICANT STINGING & BURNING | Able to detect Significantly High Alcohol Odor, as well as, a Significantly high amount of Nasal Stinging and/or Burning. The sample is sharp, and has minimal fragrance impact and/or neutral odor character. |
| 1 COMPLETE ALCOHOL ODOR SIGNIFICANT STINGING & BURNING | Able to detect Only the Alcohol Odor - No fragrance detected. Significant Nasal Stinging and/or Burning. No Alcohol Masking or Nasal Stinging & Burning alleviation. |

The alcohol-masking perfumery compounds are individually included in a test sample at 0.10% by weight of the composition. The test sample has the following composition.

| Ingredient | Weight % |
|---|---|
| SDA 40-2 alcohol (denatured with Denatonium Benzoate 0.001% v/v & t-Butyl Alcohol 0.1% v/v) | 80.000 |
| Personal care polymer* | 4.000 |
| aminomethyl propanol | 0.657 |
| dimethicone copolyol | 0.500 |

-continued

| Ingredient | Weight % |
|---|---|
| cyclomethicone | 0.240 |
| water - USP purified | QS100 |

*octylacrylamide/acrylates butylaminoethyl methacrylate copolymer (tradename Amphomer, produced by National Starch)

TRIGEMINAL NERVE STIMULATION

Without being limited by theory, it is believed that the perfumery component of the present invention provides the effect of substantially decreasing alcohol stimulation of the trigeminal (fifth cranial) nerve. The term "substantially decreases trigeminal stimulation," as used herein, means that, at a minimum, the stinging or burning sensation in the nose caused by the atomized alcohol is perceived at an equal or lesser level than the odor of the fragrance component or the natural neutral odor of the composition. This definition would correlate to an alcohol-masking potential value of about 3.0. It is believed that when the trigeminal nerve is stimulated by the atomization of high-alcohol content compositions, the burning or stinging sensation predominates over any perfumery odors which stimulate olfactory senses, e.g., the sense of smell.

It is believed that a chemical stimulant effects two different physiological responses related to the sense of smell: olfactory stimulation (e.g., the sense of smell) and trigeminal nerve stimulation. Because the two physiological responses are intimately related, great difficulty exists in differentiating and quantifying an olfactory stimulation from a trigeminal stimulation. It is known that relatively moderate to weak stimulation of the trigeminal (fifth cranial) nerve via free nerve endings in the nasal passages leads to sensations that may be confused with odor. Trygg Engen, *The Perception of Odors,* pp. 149–152 (Academic Press, Inc.) (1982), incorporated herein by reference in its entirety. In fact, a physiologist named Tucker has concluded that "the dream of finding an odorant that is purely olfactory in its stimulating capabilities is still unrealized." Tucker, D., *Handbook of Sensory Physiology. Vol IV Chemical senses* 1: *Olfaction,* pp. 151–81 (L. M. Bieldler ed., 1971), incorporated herein by reference in its entirety. It has even been suggested that even purified air, depending on its temperature and flow rate, might stimulate the trigeminal nerve. Doty et al., *Physiology and Behavior,* pp. 175–85 (1978), incorporated herein by reference in its entirety.

In general, overstimulation with any stimuli, strong odorants included, can activate the trigeminal nerve and cause varying degrees of pain. It is thought that the nerve may assume a special protective reflex against extremely high concentrations by reflexively reducing inhalation altogether, thus, cutting off all stimulation to the nostrils. Alarie, Wakisaka, & Oka, *Environmental Physiology and Biochemistry,* pp. 53–64 (1973), incorporated herein by reference in its entirety. In a test wherein the subjects were asked, on different occasions, to judge the intensity of the odor, the intensity of the "piquancy" or "burning sensation" (i.e., the trigeminal aspect), and the overall sensation, the results showed that the intensity of the odor was about two-thirds the overall intensity. Cain, *Sensory Processes,* pp. 57–67 (1977), incorporated herein by reference in its entirety. The remaining one third was accounted for as trigeminal stimulation. However, the trigeminal effect also increased at a faster rate than the olfactory, as the concentration of the odorant was increased. Cain, pp. 57–67. In other words, odor perception dominates at lower concentrations, but pain and irritation dominate at higher concentrations.

It is also believed that trigeminal nerve stimulation may inhibit olfaction. Engen, at 152. Cain and Murphy (1980) showed this by comparing the perceived intensities of various concentrations of a fruity odorant, n-amyl butyrate, and the odorless irritant, carbon dioxide. Cain and Murphy, *Perception,* pp. 459–665 (1978), incorporated herein in its entirety. Carbon dioxide is odorless but stimulates the trigeminal nerve. They tested both physical mixtures of the chemicals prepared before presenting them to the subject as dichronic mixtures, one chemical to one nostril and one to the other. In both cases, the more carbon dioxide there was in the mixture the more the irritation associated with it would inhibit the fruity odor of n-amyl butyrate, and it did so for weak and strong overall mixture concentrations. In general, "benign" odorants, such as wintergreen, anise, and cherry, were found to facilitate the olfactory bulb activity in unanesthetized monkeys, whereas trigeminal stimuli such as ammonia and acetic acid inhibited such activity. Engen, at p. 152.

PARTITION COEFFICIENT AND BOILING POINT

The alcohol-masking perfumery compound of the alcohol masking perfumery component can also be classified by its boiling point (B.P.) and its octanol/water partition coefficient (P). The octanol/water partitioning coefficient of a compound is the ratio between its equilibrium concentrations in octanol and in water. Octanol/water partitioning coefficients are well-known to chemists of ordinary skill in the art and are readily measured using standard analytical techniques or can be calculated, as described below. The alcohol-masking perfumery compounds of the present invention should not simultaneously have a B.P. (measured at the standard pressure of 1 atmosphere) of about 250° C. or higher, and an octanol/water partitioning coefficient, P, of lower than about 1,000. Because the partitioning coefficients of the perfumery compounds of this invention have high values, they are more conveniently given in the form of their logarithm to the base 10, logP. Therefore, the alcohol-masking perfumery compounds of the present invention should not simultaneously have a B.P. of about 250° C. or higher and a log P of lower than about 3.0.

The boiling points of many perfume ingredients are given in, e.g., "Perfume and Flavor Chemicals (Aroma Chemicals)," Steffen Arctander, published by the author, 1969, incorporated herein by reference.

The logP of many perfume ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf, A. Leo, in Comprehensive Medicinal Chemistry, Vol. 4, C. Hansch, P. G. Sammens, J. B. Taylor and C. A Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding.

Thus, when a high-alcohol content composition contains a perfumery compound which does not simultaneously have a B.P. of greater than about 250° C. and a logP of less than about 3, the alcohol odor and the alcohol sting to the nose are substantially reduced.

Table 1, Table 2 and Table 3 provide nonlimiting examples of perfumery compounds which do not simultaneously have a B.P. of greater than about 250° C. and a logP of less than about 3. Table 4 provides nonlimiting examples of perfumery compounds which do not substantially reduce alcohol odor and alcohol sting as they simultaneously have a B.P. of greater than about 250° C. and a logP of less than about 3. The logP values provided below have either been determined experimentally or through the use of the "CLOGP" program.

TABLE 1

Examples of Perfumery Compounds With BP > 250° C. and logP > 3.0

| Perfumery Compound | Approximate B.P. (° C.) (a) | logP |
|---|---|---|
| Allyl cyclohexane propionate | 267 | 3.935 |
| Ambrettolide | 300 | 6.261 |
| Amyl benzoate | 262 | 3.417 |
| Amyl cinnamate | 310 | 3.771 |
| Amyl cinnamic aldehyde | 285 | 4.324 |
| Amyl cinnamic aldehyde dimethyl acetal | 300 | 4.033 |
| iso-Amyl salicylate | 277 | 4.601 |
| Aurantiol | 450 | 4.216 |
| beta-methyl-3-(1-methylethyl) Benzenepropanal | 273 | 3.500 |
| Benzophenone | 306 | 3.120 |
| Benzyl salicylate | 300 | 4.383 |
| Butyl Cinnamic Aldehyde | 282 | 3.800 |
| para-tert-Butyl cyclohexyl acetate | +250 | 4.019 |
| iso-Butyl quinoline | 252 | 4.193 |
| beta-Caryophyllene | 256 | 6.333 |
| Cadinene | 275 | 7.346 |
| Cedrol | 291 | 4.530 |
| Cedryl acetate | 303 | 5.436 |
| Cedryl formate | +250 | 5.070 |
| Cinnamyl cinnamate | 370 | 5.480 |
| Cyclohexyl salicylate | 304 | 5.265 |
| Cyclamen aldehyde | 270 | 3.680 |
| Dihydro isojasmonate | +300 | 3.009 |
| Diphenyl methane | 262 | 4.059 |
| Diphenyl oxide | 252 | 4.240 |
| Dodecalactone | 258 | 4.359 |
| iso E super | +250 | 3.455 |
| Ethylene brassylate | 332 | 4.554 |
| Ethyl methyl phenyl glycidate | 260 | 3.165 |
| Ethyl undecylenate | 264 | 4.888 |
| Exaltolide | 280 | 5.346 |
| Galaxolide | +250 | 5.482 |
| Geranyl anthranilate | 312 | 4.216 |
| Geranyl phenyl acetate | +250 | 5.233 |
| Hexadecanolide | 294 | 6.805 |
| Hexenyl salicylate | 271 | 4.716 |
| Hexyl cinnamic aldehyde | 305 | 5.473 |
| Hexyl salicylate | 290 | 5.260 |
| alpha-Irone | 250 | 3.820 |
| Lilial (p-t-bucinal) | 258 | 3.858 |
| Linalyl benzoate | 263 | 5.233 |
| 2-Methoxy naphthalene | 274 | 3.235 |
| Methyl dihydrojasmone | +300 | 4.843 |
| gamma-n-Methyl ionone | 252 | 4.309 |
| Musk indanone | +250 | 5.458 |
| Musk ketone | MP = 137° C. | 3.014 |
| Musk tibetine | MP = 136° C. | 3.831 |
| Myristicin | 276 | 3.200 |
| Naphth(2,1-b)Furan, dodecahydro-3a,6,6,9a-tetramehtyl | 316 | 5.300 |
| Oxahexadecanolide-10 | +300 | 4.336 |
| Oxahexadecanolide-11 | MP = 35° C. | 4.336 |
| Para-ethyl-alpha, alpha dimethyl hydrocinnamaldehyde | 257 | 3.400 |
| Patchouli alcohol | 285 | 4.530 |

TABLE 1-continued

Examples of Perfumery Compounds With BP > 250° C. and logP > 3.0

| Perfumery Compound | Approximate B.P. (° C.) (a) | logP |
|---|---|---|
| Phantolide | 288 | 5.977 |
| Phenyl ethyl benzoate | 300 | 4.058 |
| Phenylethylphenylacetate | 325 | 3.767 |
| Phenyl heptanol | 261 | 3.478 |
| Phenyl hexanol | 258 | 3.299 |
| 2-methyl-3,-(4-tert-Butylphenyl) Propanal | 280 | 3.900 |
| cis-3-hexenyl Salicylate | 298 | 4.600 |
| alpha-Santalol | 301 | 3.800 |
| Thibetolide | 280 | 6.246 |
| delta-Undecalactone | 290 | 3.830 |
| gamma-Undecalactone | 297 | 4.140 |
| Vetiveryl acetate | 285 | 4.882 |
| Yara-yara | 274 | 3.235 |
| Ylangene | 250 | 6.268 |

TABLE 2

Examples of Perfumery Compounds With BP < 250° C. and logP < 3.0

| Perfumery Compounds | Approximate B.P. (° C.) | logP |
|---|---|---|
| Benzaldehyde | 179 | 1.480 |
| 4-methoxy Benzaldehyde | 248 | 1.800 |
| Benzyl acetate | 215 | 1.960 |
| laevo-Carvone | 231 | 2.083 |
| Geraniol | 230 | 2.649 |
| Hydroxycitronellal | 241 | 1.541 |
| cis-Jasmone | 248 | 2.712 |
| Linalool | 198 | 2.429 |
| Nerol | 227 | 2.649 |
| cis-7-decen-1-al | 128 | 2.900 |
| ethyl-2-methyl 3,4-Pentadienoate | 154 | 2.100 |
| Phenyl ethyl alcohol | 220 | 1.183 |
| alpha-Terpineol | 219 | 2.569 |

TABLE 3

Examples of Perfumery Compounds With BP < 250° C. and logP > 3.0

| Perfumery Compounds | Approximate B.P. (° C.) | logP |
|---|---|---|
| iso-Bornyl acetate | 227 | 3.485 |
| Carvacrol | 238 | 3.401 |
| cis-4-Decen-1-al | 225 | 3.500 |
| 1-Decanal | 208 | 4.000 |
| cis-6-Nonen-1-al | 225 | 3.500 |
| alpha-Citronellol | 225 | 3.193 |
| para-Cymene | 179 | 4.068 |
| Dihydro myrcenol | 208 | 3.030 |
| 2 hexyl Cyclopentanone | 220 | 3.470 |
| Geranyl acetate | 245 | 3.715 |
| d-Limonene | 177 | 4.232 |
| Undecanal | 244 | 4.100 |
| Linalyl acetate | 220 | 3.500 |
| Vertenex | 232 | 4.060 |

TABLE 4

Examples of Perfumery Compounds With BP > 250° C. and logP < 3.0

| Perfumery Compounds | Approximate B.P. (° C.) | logP |
|---|---|---|
| Coumarin | 291 | 1.412 |
| Eugenol | 253 | 2.307 |

TABLE 4-continued

Examples of Perfumery Compounds With BP > 250° C. and logP < 3.0

| Perfumery Compounds | Approximate B.P. (° C.) | logP |
| --- | --- | --- |
| iso-Eugenol | 266 | 2.547 |
| Indole | 254 decompos | 2.142 |
| Methyl cinnamate | 263 | 2.620 |
| Methyl dihydrojasmonate | +300 | 2.275 |
| Methyl-N-methyl anthranilate | 256 | 2.791 |
| beta-Methyl naphthyl ketone | 300 | 2.275 |
| delta-Nonalactone | 280 | 2.760 |
| 2,6-Nonadien-1-ol | 221 | 2.500 |
| Vanillin | 285 | 1.580 |

METHOD OF SUBSTANTIALLY DECREASING ALCOHOL STING

The present invention also relates to a method of substantially masking or reducing both the odor and the stinging or burning sensation in the nose or throat from an atomized alcohol containing composition, said method comprising the steps of (1) preparing a composition comprising: (a) from about 60% to about 99.9% by weight of said composition of alcohol, (b) from about 0.01% to about 20% by weight of said composition of a personal care polymer, and (c) from about 0.001% to about 0.3% by weight of said composition of a perfumery component which substantially masks or reduces both the odor and the stinging sensation of said alcohol in the nose or throat; and (2) atomizing said composition.

The present invention also relates to a method of substantially reducing trigeminal stimulation from an atomized alcohol containing composition, said method comprising the steps of (1) preparing a composition comprising: (a) from about 60% to about 99.9% by weight of said composition of alcohol, (b) from about 0.01% to about 20% by weight of said composition of a personal care polymer, and (c) from about 0.001% to about 0.3% by weight of said composition of a perfumery component having an Alcohol Masking Potential greater than about 2.8.; and (2) atomizing said composition.

OPTIONAL INGREDIENTS

Water can be used as an optional component in the compositions of the present invention. However, some water is included in the preferred embodiment. Typically the concentration of water can range from 0 to about 39.949% by weight of the composition.

Non-alcohol-masking Perfumery compounds which do not reduce both the alcohol odor and the alcohol sting can also be used in the compositions of the present invention. In other words, the compositions of the present invention can contain conventional fragrances. These fragrance compounds would help to impart a pleasant smelt scent, or fragrance to the composition, but would not substantially reduce the alcohol odor and the alcohol sting.

Humectants, Moisturizers, and Skin Conditioners The compositions of the present invention can optionally comprise one or more humectant, moisturizing, or skin conditioning materials. A variety of these materials can be employed and each can be present at a level of from about 0.1% to about 20%, more preferably from about 1% to about 10%, and most preferably from about 2% to about 5%. These materials include guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, to Orr et al., issued Dec. 11, 1990, which is incorporated by reference herein in its entirety.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Emulsifiers and Surfactants: The compositions of the present invention can also comprise one or more emulsifiers or surfactants. Suitable materials can include any of a wide variety of nonionic, cationic, anionic, and zwitterionic emulsifiers disclosed in the prior patents and other references. See McCutcheon's, *Detergents and Emulsifiers,* North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable compounds include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. The emulsifiers can be used individually or as a mixture of two or more and comprise from about 0.1% to about 10%, more preferably from about 0.15% to about 7%, and most preferably from about 0.25% to about 5% of the compositions of the present invention.

Cosmetic or Pharmaceutical Active Ingredients

The compositions of the present invention can comprise a safe and effective amount of one or more cosmetic or pharmaceutical active ingredients.

The term "safe and effective amount" as used herein, means an amount of an active ingredient high enough to modify the condition to be treated or to deliver the desired benefit, but low enough to avoid serious side effects, at a reasonable benefit to risk ratio within the scope of sound medical judgment. What is a safe and effective amount of the active ingredient will vary with the specific active, the ability of the active to penetrate through the skin, the mucosa, or into the hair, the age and health condition, of the user, and the intended purpose of the product, i.e. cosmetic or pharmaceutical.

The active ingredients useful herein can be categorized by their cosmetic or therapeutic benefit or their postulated mode of action. However, it is to be understood that the active ingredients useful herein can in some instances provide more than one cosmetic or therapeutic benefit or operate via more than one mode of action. Therefore, classifications herein are made for the sake of convenience and are not intended to limit the active ingredient to that particular application or applications listed. Also, pharmaceutically-acceptable salts and derivatives of these active ingredients are useful herein. The following active ingredients are useful in the compositions of the present invention.

Anti-Acne Actives: Examples of useful anti-acne actives include the keratolytics such as salicylic acid (o-hydroxbenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives: Examples of antiwrinkle and anti-skin atrophy actives include retinoic acid and its derivatives (e.g., cis and trans); retinol; retinyl esters; niacinamide, salicylic acid and derivatives thereof, sulfur-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid, and skin peel agents (e.g., phenol and the like).

Non-Steroidal Anti-Inflammatory Actives (NSAIDS): Examples of NSAIDS include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics: Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketarine, pramoxine, phenol, and pharmaceutically acceptable salts thereof.

Artificial Tanning Agents and Accelerators. Examples of artificial tanning agents and accelerators include dihydroxyacetaone, tyrosine, tyrosine esters such as ethyl tyrosinate, and phospho-DOPA.

Sunscreen Actives: Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Non-limiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. Especially preferred examples of these sunscreens include those selected from the group consisting of 4-N,N-(2-ethylhexyl) methylaminobenzoic acid ester of 2,4-dihydroxybenzophenone, 4N,N-(2-ethylhexyl) methylaminobenzoic acid ester with 4-hydroxydibenzoylmethane, 4-N,N- (2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreens which can be employed will vary depending upon the sunscreen chosen and the desired Sun Protection Factor (SPF) to be achieved. SPF is a commonly used measure of photoprotection of a sunscreen against erythema. See *Federal Register* VoL 43, No. 166, pp. 38206–38269, Aug. 25, 1978, which is incorporated herein by reference in its entirety.

Antimicrobial and Antifungal Actives: Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfte, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netumicin sulfate, paromomycin sulfate, streptomycin sulfate, tobramycin te, miconazole hydrochloride, amanfadine hydrochloride, amantadine sulfate, octopirox, parachirometa xylenol, nystatin, tolnaftate, zinc pyrithione and clotrimazole.

Preferred examples of actives useful herein include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-Cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, and mixtures thereof.

Antihistaminics: Useful herein are antihistaminic drug active. Antihistaminic drugs preferred for inclusion in compositions of the present invention include pharmaceutically-acceptable salts of chlorpheniramine, triprolidine, diphenhydramine, doxylamine, pyrilamine, phenindamine, promethazine, cyproheptadine, azatadine, clemastine, carbinoxamine, tripelennamine, terfenadine, dexchlorpheniramine, brompheniramine, chlorcyclizine, diphenylpyraline, pheniramine, phynyltoloxamine, and mixtures thereof.

Antitussives: Useful herein are antitussive drug actives. Antitussive drugs preferred for inclusion in compositions of the present invention include pharmaceutically-acceptable salts of dextromethorphan, codeine, caramiphen, chlopedianol noscapine, diphenhydramine, codeine, hydrocodone, hydromorphone, and carbetapentane.

Antiprnritics: Useful herein are antipruritic drug actives. Antipruritic drugs preferred for inclusion in compositions of the present invention include pharmaceutically-acceptable salts of methdilizine and trimeprazine.

Decongestants: Useful herein are decongestant drug actives. Decongestant drugs preferred for inclusion in compositions of the present invention include pharmaceutically-acceptable salts of pseudoephedrine, phenylpropanolamine, phenylephrine and ephedrine.

Expectorants: Useful herein are expectorant drug actives. Examples of useful expectorants (also known as mucolytic agents) include; glyceryl guaiacolate, terpin hydrate, ammonium chloride, N-acetylcysteine, and ambroxol, their pharmaceutically acceptable salts, and mixtures thereof.

Analgesics: Useful herein are analgesic drug actives. Examples of useful analgesics include; morphine, codeine, meperidine, pentazocine, propoxyphene, acetaminophen, allopurinol, acetylsalicylic acid, choline salicylate, ketoprofen, magnesium silicate, salsalate, fenoprofen, ibuprofen, indomethacin, naproxen, and many others and their pharmaceutically acceptable salts and mixtures thereof.

Analgesics, decongestants, expectorants and antitussives, as well as their acceptable dosage ranges are described in U.S. Pat No. 4,783,465 to Sunshine et al., issued Nov. 8, 1988, and U.S. Pat No. 4,619,934 to Sunshine et al., issued Oct. 28, 1986, which are incorporated by reference herein.

Cough Suppressants: Useful herein are anticough drug actives. Anticough drugs preferred for inclusion in compositions of the present invention include pharmaceutically-acceptable salts dextromethorphan, codeine, caramiphen, carbetapentane, chlophedianol, noscapine, diphenhydramine, hydrocodone and hydromorphone.

Anti-cholinergics: Useful herein are anticholinergic drug actives. Anticholinergic drugs preferred for inclusion in compositions of the present invention include pharmaceutically-acceptable salts of scopolamine, atropine, homatropine, levodopa, dicyclomine, hyoscaaunne, procyclidine, trihexyphenidyl and ethopropazine.

Nonlimiting examples of preferred actives useful herein include those selected from the group consisting of salicylic acid, benzoyl peroxide, niacinamide, cis-retinoic acid, trans-retinoic acid, retinol, retinyl palmitate, phytic acid, N-acetyl L-cysteine, azelaic acid, lipoic acid, resorcinol, lactic acid, glycolic acid, ibuprofen, naproxen, hydrocortisone, phenoxyethanol phenoxypropanol, phenoxyisopropanol, 2,4,4,'-trichloro-2'-hydroxy diphenyl ether, 3,4,4'-trichlorocarbanilide, 2-ethylhexyl p-methoxycinnamic acid, oxybenzone, 2-phenylbenzimidozole-5-sulfonic acid, dihydroxyacetone, and mixtures thereof. Let's expand this list based on what else we add.

Other Optional Components

The compositions of the present invention can comprise a wide range of other optional components. These additional components should be cosmetically or pharmaceutically acceptable, depending upon the intended use. The *CTFA Cosmetic Ingredient Handbook,* Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, absorbents, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, skin-conditioning agents (humectants, miscellaneous, and occlusive).

Some nonlimiting examples of these additional components cited in the *CTFA Cosmetic Ingredient Handbook,* as well as other materials useful herein, include the following: vitamins and derivatives thereof (e.g. tocopherol, tocopherol acetate, retinoic acid, retinol, retinoids, and the like); polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; other anti-acne medicaments (e.g., resorcinol, sulfur, salicylic acid, erythromycin, zinc, and the like); skin bleaching (or lightening) agents including but not limited to hydroquinone, kojic acid; antioxidants; chelators and sequestrants; skin treating agents such as alpha-hydroxy acids such as lactic acid and glycolic acid, and aesthetic components such as fragrances, pigments, colorings, essential oils, skin sensates, astringents, skin soothing agents, skin healing agents and the like, Nonlimiting examples of these aesthetic components include panthenol and derivatives (e.g. ethyl panthenol), aloe vera, pantothenic acid and its derivatives, clove oil, menthol camphor, eucalyptus oil, eugenol, menthyl lactate, witch hazel distillate, allantoin, bisabolol and dipotassium glycyrrhizinate.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES I–IV
Deodorant Spray Compositions

| Ingredient | I WT. % | II WT. % | III WT. % | IV WT. % |
|---|---|---|---|---|
| Ethanol | 80.6 | 67.0 | 60.0 | 70.6 |
| Isopropanol | — | — | 7.0 | 10.0 |
| D-5 Cyclomethicone | 2.0 | — | 2.0 | 2.0 |
| Zinc Phenolsulfonate | — | 1.0 | 1.0 | 1.0 |
| PPG-3 Myrisyl Ether | — | 15.0 | 15.0 | 15.0 |
| Dimethicone[1] | 1.0 | 1.0 | 1.0 | 1.0 |
| Cis-3-Hexenyl Salicylate | 0.003 | 0.006 | 0.009 | 0.03 |
| para-Ethyl-alpha, alpha-Dimethyl Hydrocinnamaldehyde | 0.002 | 0.004 | 0.006 | 0.02 |
| 2-methyl-3-(4-tert-butylphenyl) propanal | 0.018 | 0.036 | 0.054 | 0.18 |
| Dipropylene Glycol | 0.0053 | 0.011 | 0.0159 | 0.053 |
| 3,7-Dimethyl-2,6-Octadien-1-01 | 0.0005 | 0.001 | 0.0015 | 0.005 |
| Cyclo-1,13-ethlenedioxytridecan-1,13-dione | 0.005 | 0.010 | 0.015 | 0.05 |
| Water | QS100 | QS100 | QS100 | QS100 |

[1]Dow Corning 200 Fluid - 20 cs

The above compositions are prepared by combining the listed ingredients in a suitable vessel using standard mixing techniques. The final product is packaged in a conventional non-aerosol pump spray container or in an aerosol canister with a suitable propellant.

When sprayed or atomized, these products substantially mask or reduce both the odor and the stinging sensation of the alcohol in the nose or throat.

EXAMPLES V–VIII
After Shave/Cologne Compositions

| Ingredient | V WT. % | VI WT. % | VII WT. % | VIII WT. % |
|---|---|---|---|---|
| Ethanol | 61.55 | 79.30 | 74.30 | 60.00 |
| Isopropanol | — | — | 5.00 | 10.00 |
| Benzophenone | 0.10 | 0.10 | 0.10 | 0.10 |
| Dimethicone[1] | 0.2 | 0.2 | 0.2 | 0.2 |
| Cis-3-Hexenyl Salicylate | 0.003 | 0.006 | 0.03 | 0.015 |
| para-Ethyl-alpha, alpha-Dimethyl Hydrocinnamaldehyde | 0.002 | 0.004 | 0.02 | 0.01 |
| 2-methyl-3-(4-tert-butylphenyl) propanal | 0.018 | 0.036 | 0.18 | 0.09 |
| Dipropylene Glycol | 0.0053 | 0.011 | 0.053 | 0.0265 |
| 3,7-Dimethyl-2,6-Octadien-1-01 | 0.0005 | 0.001 | 0.005 | 0.0025 |
| Cyclo-1,13-ethlenedioxytridecan-1,13-dione | 0.005 | 0.010 | 0.05 | 0.025 |
| Water | QS100 | QS100 | QS100 | QS100 |

[1]Dow Corning 200 Fluid - 20 cs

The above compositions are prepared by combining the listed ingredients in a suitable vessel using standard mixing techniques. The final product is packaged in a conventional non-aerosol pump spray container or in an aerosol canister with a suitable propellant.

When sprayed or atomized, these products substantially mask or reduce both the odor and the stinging sensation of the alcohol in the nose or throat.

EXAMPLES IX–XII
Hair Spray Compositions

| Ingredient | IX WT. % | X WT. % | XI WT. % | XII WT. % |
|---|---|---|---|---|
| Ethanol (denatured with Denatonium Benzoate 0.001% v/v & t-Butyl Alcohol 0.1% v/v) | 80.000 | 74.000 | 74.000 | 78.000 |
| Isopropanol | — | — | 6.000 | 2.000 |
| Octylacrylamide/Acrylates Butylaminoethyl Methacrylate Copolymer[1] | 4.000 | 4.000 | 4.000 | 4.000 |
| Aminomethyl Propanol | 0.657 | 0.657 | 0.657 | 0.657 |
| Dimethicone Copolyol[2] | 0.500 | 0.500 | 0.500 | 0.500 |
| Cyclomethicone D4 | 0.240 | 0.240 | 0.240 | 0.240 |
| Cis-3-Hexenyl Salicylate | 0.003 | 0.006 | 0.009 | 0.0015 |
| para-Ethyl-alpha, alpha-Dimethyl Hydrocinnamaldehyde | 0.002 | 0.004 | 0.008 | 0.001 |
| 2-methyl-3-(4-tert—butylphenyl) propanal | 0.018 | 0.036 | 0.052 | 0.009 |
| Dipropylene Glycol | 0.0053 | 0.011 | 0.0159 | 0.0026 |
| 3,7-Dimethyl-2,6-Octadien-1-01 | 0.0005 | 0.001 | 0.0015 | 0.00025 |
| Cyclo-1,13-ethlenedioxytridecan-1,13-dione | 0.005 | 0.010 | 0.015 | 0.0025 |
| Water | QS100 | QS100 | QS100 | QS100 |

[1]Tradename Amphomer, produced by National Starch
[2]Dow Corning DC193

The above compositions are prepared by combining the listed ingredients in a suitable vessel using standard mixing techniques. The final product is packaged in a conventional non-aerosol pump spray container or in an aerosol canister with a suitable propellant.

When sprayed or atomized, these products substantially mask or reduce both the odor and the stinging sensation of the alcohol in the nose or throat.

Alternatively, the above compositions can be made by substituting Octylacrylamide/Acrylates Butylaminoethyl Methacrylate copolymer with Acrylates/Dimethicone crosspolymer produced by Mitsubishi Chemical Company.

EXAMPLES XIII–XVI
Topical Analgesic Compositions

| Ingredient | XIII WT. % | XIV WT. % | XV WT. % | XVI WT. % |
|---|---|---|---|---|
| Ethanol | 60.0 | 70.0 | 65.0 | 70.0 |
| Isopropanol | — | — | 4.0 | 3.0 |
| PEG-4 | 5.000 | 5.000 | 5.000 | 5.000 |
| PPG-11 Stearyl Ether | 2.000 | 2.000 | 2.000 | 2.000 |
| Methyl Salicylate | 2.000 | 2.000 | 2.000 | 2.000 |
| Disodium EDTA | 0.010 | 0.010 | 0.010 | 0.010 |
| Dimethicone Copolyol[1] | 0.50 | 0.50 | 0.50 | 0.50 |
| Cis-3-Hexenyl Salicylate | 0.003 | 0.006 | 0.009 | 0.03 |
| para-Ethyl-alpha, alpha-Dimethyl Hydrocinnamaldehyde | 0.002 | 0.004 | 0.006 | 0.02 |
| 2-methyl-3-(4-tert-butylphenyl) propanal | 0.018 | 0.036 | 0.054 | 0.18 |
| Dipropylene Glycol | 0.0053 | 0.011 | 0.016 | 0.053 |
| 3,7-Dimethyl-2,6-Octadien-1-01 | 0.0005 | 0.001 | 0.0015 | 0.005 |
| Cyclo-1,13-ethlenedioxytridecan-1,13-dione | 0.005 | 0.010 | 0.015 | 0.05 |
| Water | QS100 | QS100 | QS100 | QS100 |

[1]Dow Corning DC193

The above compositions are prepared by combining the listed ingredients in a suitable vessel using standard mixing techniques. The final product is packaged in a conventional non-aerosol pump spray container or in an aerosol canister with a suitable propellant.

When sprayed or atomized, these products substantially mask or reduce both the odor and the stinging sensation of the alcohol in the nose or throat.

EXAMPLES XVII–XX
Topical Anteseptic Compositions

| Ingredient | XVII WT. % | XVIII WT. % | XIX WT. % | XX WT. % |
|---|---|---|---|---|
| Ethanol | 60.0 | 61.0 | 65.0 | 70.0 |
| Isopropanol | — | 4.0 | 5.0 | 5.0 |
| PEG-4 | 5.000 | 5.000 | 5.000 | 5.000 |
| PPG-11 Stearyl Ether | 2.000 | 2.000 | 2.000 | 2.000 |
| Triclosan | 2.000 | 2.000 | 2.000 | 2.000 |
| Disodium EDTA | 0.010 | 0.010 | 0.010 | 0.010 |
| Hydroxyethyl Cellulose[1] | 0.10 | 0.10 | 0.10 | 0.10 |
| Cis-3-Hexenyl Salicylate | 0.003 | 0.006 | 0.009 | 0.03 |
| para-Ethyl-alpha, alpha-Dimethyl Hydrocinnamaldehyde | 0.002 | 0.004 | 0.008 | 0.02 |
| 2-methyl-3-(4-tert-butylphenyl) propanal | 0.018 | 0.036 | 0.054 | 0.18 |
| Dipropylene Glycol | 0.0053 | 0.011 | 0.0159 | 0.053 |
| 3,7-Dimethyl-2,6-Octadien-1-01 | 0.0005 | 0.001 | 0.0015 | 0.005 |
| Cyclo-1,13-ethlenedioxytridecan-1,13-dione | 0.005 | 0.010 | 0.015 | 0.05 |
| Water | QS100 | QS100 | QS100 | QS100 |

[1]Natrosol 250L (Aqualon)

The above compositions are prepared by combining the listed ingredients in a suitable vessel using standard mixing techniques. The final product is packaged in a conventional non-aerosol pump spray container or in an aerosol canister with a suitable propellant.

When sprayed or atomized, these products substantially mask or reduce both the odor and the stinging sensation of the alcohol in the nose or throat.

EXAMPLES XXI–XXIV
Astringent Compositions

| Ingredient | XXI WT. % | XXII WT. % | XXIII WT. % | XXIV WT. % |
|---|---|---|---|---|
| Ethanol | 60.000 | 65.000 | 70.000 | 60.000 |
| Isopropanol | — | — | 4.000 | 2.000 |
| PEG-4 | 5.000 | — | 5.000 | 5.000 |
| PPG-11 Stearyl Ether | 2.000 | — | 2.000 | 2.000 |
| Salicylic Acid | 2.000 | 2.000 | 2.000 | 2.000 |
| Hydroxyethyl Cellulose[1] | 0.10 | 0.10 | 0.10 | 0.10 |
| Disodium EDTA | 0.010 | 0.005 | 0.005 | 0.005 |
| Triethanolamine | — | 0.660 | 0.660 | 0.660 |
| Menthol | — | 0.100 | 0.100 | 0.100 |
| Dimethicone[2] | — | 1.000 | 1.000 | 1.000 |
| Cis-3-Hexenyl Salicylate | 0.003 | 0.006 | 0.03 | 0.015 |
| para-Ethyl-alpha, alpha-Dimethyl Hydrocinnamaldehyde | 0.002 | 0.004 | 0.02 | 0.01 |
| 2-methyl-3-(4-tert-butylphenyl) propanal | 0.018 | 0.036 | 0.18 | 0.09 |
| Dipropylene Glycol | 0.0053 | 0.011 | 0.053 | 0.027 |
| 3,7-Dimethyl-2,6-Octadien-1-01 | 0.0005 | 0.001 | 0.005 | 0.0025 |
| Cyclo-1,13-ethlenedioxytridecan-1,13-dione | 0.005 | 0.010 | 0.05 | 0.025 |
| Water | QS100 | QS100 | QS100 | QS100 |

[1]Natrosol 250L (Aqualon)
[2]Dow Corning 200 Fluid - 20 cs

The above compositions are prepared by combining the listed ingredients in a suitable vessel using standard mixing techniques. The final product is packaged in a conventional non-aerosol pump spray container or in an aerosol canister with a suitable propellant.

When sprayed or atomized, these products substantially mask or reduce both the odor and the stinging sensation of the alcohol in the nose or throat.

What is claimed is:

1. A composition for use on the skin, hair or mucosa comprising:
    (a) from about 60% to about 99.9% by weight of said composition of alcohol,
    (b) from about 0.01% to about 20% by weight of said composition of a personal care polymer, and
    (c) from about 0.001% to about 0.3% by weight of said composition of a perfumery component wherein the perfumery component does not simultaneously have a boiling point of about 250° C. or higher and the natural log of its octanol/water partition coefficient of lower than about 3.0,
wherein said composition is sprayed or atomized upon use.

2. A composition according to claim 1 wherein said alcohol comprises from about 65% to about 85% by weight of said composition, said personal care polymer comprises from about 0.05% to about 15% by weight of said composition, and said perfumery component comprises from about 0.01% to about 0.25% by weight of said composition.

3. A composition according to claim 1 wherein said alcohol comprises from about 70% to about 85% by weight of said composition, said personal care polymer comprises from about 0.1% to about 10% by weight of said composition, and said perfumery component comprises from about 0.05% to about 0.2% by weight of said composition.

4. A composition according to claim 1 wherein said alcohol is selected from the group consisting of ethanol, n-propanol, iso-propanol, and mixtures thereof.

5. A composition according to claim 4 wherein said alcohol is ethanol.

6. A composition according to claim 4 wherein said perfumery component comprises one or more compounds selected from the group consisting of C2–C20 aldehydes, C5–C15 esters, C4–C15 alcohols, C4–C20 ethers, C3–C15 ketones, and mixtures thereof.

7. A composition according to claim 6 wherein said perfumery component comprises one or more compounds selected from the group consisting of C7–C15 aldehydes, C8–C13 esters, C4–C10 alcohols, a C14–C17 ethers, C9–C12 ketones, and mixtures thereof.

8. A composition according to claim 6 wherein said C2–C20 aldehyde is selected from the group consisting of beta-methyl-3-(1-methylethyl) benzenepropanal; phenoxy acetaldehyde; 1-nonanal; 2-methyl undecanal methyl nonyl acetaldehyde; 3,7dimethyl-2-methylene-6-octenal; phenoxy acetaldehyde; 3-cyclohexene-1carbox-aldehyde,4-(4-hydroxy 4 methyl pentyl); phenoxy acetaldehyde; alpha-n-hexyl cinnamic aldehyde; 2-norpinene-2-propionaldehyde, 6,6-dimethyl; 3-cyclohexene-1-carbox-aldehyde; 1-methyl-4-(4-methyl-3-penenyl); 10-undecenal; 3-cyclohexene-1carbox-aldehyde,4-(4-hydroxy-4-methyl pentyl); 4,7-methyanoindan-1-carboxaldehyde; hexahydro; benzaldehyde; 2,6-dimethyl-5-hepten-1-al; 2-methyl-3-(4-isopropylphenyl)propanal; and mixtures thereof.

9. A composition according to claim 6 wherein said C5–C15 ester is selected from the group consisting of benzyl ortho hydroxy benzoate; phenyl ortho hydroxy benzoate; 2-buten-1-ol3-methyl:acetate; 2-propenyl-3-cyclohexylpropanoate; allyl hexanoate; 9-hexadecenolide; hexyl salicylate; methyl 2,4-decadienoate; methyl 3-nonenoate; 9-decen-1-yl acetate; and mixtures thereof.

10. A composition according to claim 6 wherein said C4–C15 alcohol is selected from the group consisting of beta gamma hexenol; 3,7mimethyl-2,6-octadien-1-ol; 2,4-dimethyl-3-cyclohexene-1-methanol; 1-pentanol,3-methyl-5-5-phenyl; 2-phenyl ethyl alcohol; 9-decen-1-ol; 2-methyl-3-phenylpropan-2-ol; 4-methyl-3-decen-5-ol; and mixtures thereof.

11. A composition according to claim 6 wherein said C4–C20 ether is selected from the group consisting of 2-ethyl furan; hydrocinnamaldehyde; alpha-methyl-3,4-(methylenedioxy); 2-pentyl furan; 2-(6-methyl-8-(1-methylethyl)bicuclo<2.2.2.>oct-5-ene-2-(or3)yl-1,3-dioxolane; and mixtures thereof.

12. A composition according to claim 6 wherein said C3–C15 ketone is selected from the group consisting of oxacycloheptadean-2-one; gamma - undecalactone; 3-methyl-5-propyl-2-cyclohexen-1-one; 4-nonanolide; ethyl amyl ketone; 3-hepten-2one; methyl dihrojasmonate; 3-decen-2-one; geranyl cyclopentanone; dihydro alpha ion-one; 4-(2,6,6-trimethyl-2-cyclohexen-1-yl)-3-methyl-3-butene-2-one; and mixtures thereof.

13. A composition according to claim 6 wherein said perfumery component comprises one or more compounds selected from the group consisting of beta-methyl-3-(1-methylethyl) benzenepropanal; cis-4-decen-1-al; cis-7-decen-1-al; cis-6-nonen-1-al; undecanal; para-ethyl-alpha, alpha dimenthyl hydrocinnamaldehyde; butyl cinnamic aldehyde; 2-methyl-3,-(4-tert-butylphynyl) propanal; 4-methoxy benzaldehyde; decyl aldehyde; 2-hexyl cyclopentanone; ethyl-2-methyl 3,4-pentadienoate; cis-3-hexenyl salicylate; 2,6-nonadien-1-ol; napth(2,1-b)furan, decodecahydro-3a,6,6,9a-tetramethyl; and mixtures thereof.

14. A composition according to claim 6 wherein said personal care polymer is selected from the group consisting of gums; resins; proteins; polysaccharides; carboxylic acid polymers; polyacrylates; polyacrylamides; silicones; silicone copolymers; vinyl ether/maleic anhydride copolymers; poly (N-vinylpyrolidones); and mixtures thereof.

15. A composition according to claim 14 wherein said personal care polymer is selected from the group consisting of xanthan gum; guar gum; myristoyl hydrolized collagen; polyacrylic acids; acrylates/C10–C30 alkyl acrylate crosspolymers; homopolymers of acrylic acid crosslinked with an allyl ether of pentaerylthriotol; an allyl ether of sucrose; or an allyl ether of propylene; polyacrylic acids; vinyl acetatet/crotonates copolymer, vinyl acetate/crotonates/vinyl neadecanoate copolymers; octylacrylamide/acrylates/butylaminoethyl methacrylate copolymers; polyvinylpyrrolidone/vinyl acetate copolymers; polyquaternium 10 through 30; PVM/MA copolymers; PVM/VA decadiene crosspolymers; butyl ester of PVM/MA copolymers; ethyl ester of PVM/MA copolymers; isopropyl ester of PVM/MA copolymers; polyvinyl methyl ether polymers; stearylvinyl ether/MA copolymers; acrylates/dimethicone crosspolymers; and mixtures thereof.

16. A method of substantially masking or reducing both the odor and the stinging sensation in the nose or throat from an atomized alcohol containing composition, said method comprising the steps of:

(1) preparing a composition comprising:
  (a) from about 60% to about 99.9% by weight of said composition of alcohol,
  (b) from about 0.01% to about 20% by weight of said composition of a personal care polymer, and
  (c) from about 0.001% to about 0.3% by weight of said composition of a perfumery component wherein the perfumery component does not simultaneously have a boiling point of about 250° C. or higher and the natural log of its octanol/water partition coefficient of lower than about 3.0, and (2) application of said composition by atomizing or spraying to the skin, hair, or mucosa of a human in need of such treatment.

17. A method of substantially reducing trigeminal stimulation from an atomized alcohol containing composition, said method comprising the steps of:

(1) preparing a composition comprising:
  (a) from about 60% to about 99.9% by weight of said composition of alcohol,
  (b) from about 0.01% to about 20% by weight of said composition of a personal care polymer, and
  (c) from about 0.001% to about 0.3% by weight of said composition of a perfumery component wherein the perfumery component does not simultaneously have a boiling point of about 250° C. or higher and the natural log of its octanol/water partition coefficient of lower than about 3.0, and (2) application of said composition by atomizing or spraying to the skin, hair, or mucosa of a human in need of such treatment.

* * * * *

UNITED STATES PATENT AND TRADEMARK OFFICE
CERTIFICATE OF CORRECTION

PATENT NO.   : 6,126,930
DATED        : October 3, 2000
INVENTOR(S)  : Z.G. Dubois et al.

It is certified that error appears in the above-identified patent and that said Letters Patent is hereby corrected as shown below:

Column 33,
Line 20, "3-cyclohexene-1carbox-aldehyde,4-(4-hydroxy-4-methyl pentyl)" should read -- 3-cyclohexene-1-carbox-aldehyde,4-(4-hydroxy-4-methyl pentyl) --.
Line 28, "2-buten-1-o13-methyl:acetate;" should read -- 2-buten-1-o1,3-methyl:acetate; --.
Line 34, "3,7mimethyl-2,6-octadien-1-o1;" should read -- 3,7dimethyl-2,6-octadien-1-o1; --.

Column 34,
Line 14, "acetatet/crotonates" should read -- acetate/crotonates --.

Signed and Sealed this

Twenty-second Day of March, 2005

JON W. DUDAS
*Director of the United States Patent and Trademark Office*